(12) United States Patent
Ferree

(10) Patent No.: US 6,648,918 B2
(45) Date of Patent: Nov. 18, 2003

(54) TREATING DEGENERATIVE DISC DISEASE THROUGH THE TRANSPLANTATION OF DEHYDRATED TISSUE

(76) Inventor: Bret A. Ferree, 1238 Cliff Laine Dr., Cincinnati, OH (US) 45208

( * ) Notice: Subject to any disclaimer, the term of this patent is extended or adjusted under 35 U.S.C. 154(b) by 0 days.

(21) Appl. No.: 10/143,637

(22) Filed: May 10, 2002

(65) Prior Publication Data

US 2002/0133231 A1 Sep. 19, 2002

Related U.S. Application Data

(63) Continuation-in-part of application No. 09/639,309, filed on Aug. 14, 2000, now Pat. No. 6,419,702.
(60) Provisional application No. 60/148,913, filed on Aug. 13, 1999.

(51) Int. Cl.$^7$ .................................................. A61F 2/44
(52) U.S. Cl. ................................ 623/17.11; 623/17.16; 424/93.7
(58) Field of Search ........................... 627/17.11–17.16, 627/919, 908; 424/93.7

(56) References Cited

U.S. PATENT DOCUMENTS

| | | | |
|---|---|---|---|
| 4,695,536 A | 9/1987 | Lindstrom et al. | 435/1 |
| 4,873,186 A | 10/1989 | Chen et al. | 435/1 |
| 5,514,180 A | 5/1996 | Heggeness et al. | 623/17.11 |
| 5,545,229 A | 8/1996 | Parsons et al. | 623/17.11 |
| 6,060,053 A | 5/2000 | Atala | 424/93.7 |
| 6,077,987 A | 6/2000 | Breitbart et al. | 623/11.11 |
| 6,177,259 B1 * | 1/2001 | Yuan et al. | 435/23 |
| 6,187,048 B1 * | 2/2001 | Milner et al. | 623/17.12 |
| 6,197,586 B1 | 3/2001 | Bhatnagar et al. | 435/395 |
| 6,231,615 B1 | 5/2001 | Preissman | 623/23.73 |
| 6,352,557 B1 * | 3/2002 | Ferree | 623/17.11 |
| 6,402,784 B1 * | 6/2002 | Wardlaw | 623/17.11 |
| 6,419,702 B1 * | 7/2002 | Ferree | 623/17.11 |
| 6,482,234 B1 * | 11/2002 | Weber et al. | 623/17.12 |
| 6,540,741 B1 * | 4/2003 | Underwood et al. | 606/32 |

OTHER PUBLICATIONS

Kayama S et al.; "Cultured, autologous nucleus pulpous cells induce functional changes in spinal nerve roots" PINE Oct. 15, 1998;23(20):2155–8.*
Okuma M, Mochida et al. "Reinsertion of stimulated nucleus pulposus cells retards intervertebral disc degeneration:an in vitro and in vivo experimental study"; J ORTHOP RES. Nov. 2000;18(6):988–97.*
Lumbar Intervertebral Disc Transfer a Canine Study, Steven L. Frick MD, et al. Spine vol. 19, No. 16, pp. 1826–1835.
Orthopedics today, Jul. 2000 "Proceedings 13th Annual Meeting" North American Spine Society, Oct. 1998 "Proceedings 14th Annual Meeting" North American Spine Society, Oct. 1999.

* cited by examiner

Primary Examiner—David H. Willse
Assistant Examiner—Suzette J. Jackson
(74) Attorney, Agent, or Firm—Gifford, Krass, Groh, Sprinkle, Anderson & Citkowski, PC

(57) ABSTRACT

A method of treating a diseased or traumatized intervertebral disc is based upon the transplantation of one or more dehydrated biologic tissues into the disc space. In the preferred embodiment, dehydrated nucleus pulposis tissue is used, which may be combined with live nucleus cells. The dehydration allows the insertion of the transplanted cells and/or tissue through a smaller annular hole. Dehydration also decreases the volume of the material transferred, thus allowing the surgeon to insert more into the disc space. Once in the body, the materials hydrate by imbibing fluid from the surrounding area. In the case of nucleus pulposis tissue, the subsequent hydration helps to restore disc height and help prevent extrusion of disc material through the hole in the annulus. One or more therapeutic substances may be added, including culture media, growth factors, differentiation factors, hydrogels, polymers, antibiotics, anti-inflammatory medications, or immunosuppressive medications. These additional substances may or may not be dehydrated as well, depending upon efficacy, initial versus final volume, and so forth.

7 Claims, No Drawings

TREATING DEGENERATIVE DISC DISEASE THROUGH THE TRANSPLANTATION OF DEHYDRATED TISSUE

REFERENCE TO RELATED APPLICATIONS

This application is a continuation-in-part of U.S. patent application Ser. No. 09/639,309, filed Aug. 14, 2000 now Pat. No. 6,419,702, which claims priority of U.S. Provisional Patent Application Serial No. 60/148,913, filed Aug. 13, 1999, the entire content of both being incorporated herein by reference.

FIELD OF THE INVENTION

This invention relates generally to the treatment of diseased or traumatized intervertebral discs, and more particularly, to transplantation of transplantation of dehydrated tissue including nucleus pulposis in conjunction with such treatment.

BACKGROUND OF THE INVENTION

Intervertebral discs provide mobility and a cushion between the vertebrae. At the center of each disc is the nucleus pulposus which, in the adult human, is composed of cells and an insoluble extracellular matrix which is produced by the nucleus itself. The extracellular matrix is composed of collagen, proteoglycans, water, and noncollagenous proteins. The nucleus pulposus is surrounded by the annulus fibrosis, which is composed of cells (fibrocyte-like and chondrocyte-like), collagen fibers, and non-fibrillar extracellular matrix. The components of the annulus are arranged in 15–25 lamellae around the nucleus pulposus.

The cells of the nucleus pulposus have chondrocyte-like features. In an adult human, the cells of the nucleus pulposis obtain nutrients and eliminate waste by diffusion through blood vessels in the endplates of the vertebrae adjacent to the disc. Blood vessels do not course into the nucleus pulposis. The relative vascular isolation of the nucleus pulposis imparts isolation of nucleus pulposis cells from the body's immune system.

To date, the treatment of degenerative disc disease has relied for the most part on eliminating the defective disc or disc function. This may be accomplished by fusing the vertebra on either side of the disc. In terms of replacement, most prior-art techniques use synthetic materials to replace the entire disc or a portion thereof. My pending U.S. patent application Ser. No. 09/415,382 discloses disc replacement methods and apparatus using synthetic materials.

Unfortunately, disc replacement using synthetic materials does not restore normal disc shape, physiology, or mechanical properties. Synthetic disc replacements tend to wear out, resulting in premature failure. The problems associated with the wear of prosthetic hip and knees are well known to those skilled in orthopedic surgery. The future of treating degenerative disc disease therefore lies in treatments which preserve disc function. If disc function could be restored with biologic replacement or augmentation, the risk of premature wearout would be minimized, if not eliminated.

SUMMARY OF THE INVENTION

This invention is directed to a method of treating a diseased or traumatized intervertebral disc through the transplantation of one or more dehydrated biologic tissues into the disc space. In the preferred embodiment, dehydrated nucleus tissue is used, which may be combined with extracellular matrix materials.

Broadly according to the method, live biologic tissue is harvested from a human or animal donor. The tissue is dehydrated, after which the harvested tissue is introduced into the disc being treated through a hole formed in the annulus fibrosis. Dehydration allows the insertion of the transplanted cells and/or tissue through a smaller annular hole. Dehydration also decreases the volume of the material transferred, thus allowing the surgeon to insert more into the disc space. Once in the body, the materials hydrate by imbibing fluid from the surrounding area. In the case of nucleus pulposis tissue, the subsequent hydration helps to restore disc height and help prevent extrusion of disc material through the hole in the annulus.

A preferred embodiment includes the step of harvesting nucleus pulposis cells, with or without extracellular matrix material, dehydrating and morselizing the cells and/or tissues. A passageway is formed through the annulus fibrosis, and the dehydrated components are introduced into the disc through the passageway using, for example, a needle and syringe or small cannula. Alternatively the step of transplanting may include percutaneously or laparoscopically injecting the dehydrated constituents into the disc being treated. Nucleus cells are added to the dehydrated tissue at the time of insertion.

One or more therapeutic substances may be added, including culture media, growth factors, differentiation factors, hydrogels, polymers, antibiotics, anti-inflammatory medications, or immunosuppressive medications. These additional substances may or may not be dehydrated as well, depending upon efficacy, initial versus final volume, and so forth.

DETAILED DESCRIPTION OF THE INVENTION

As discussed above, this invention resides in a method of treating a diseased or traumatized intervertebral disc through the transplantation of one or more dehydrated biologic tissues into the disc space. In the preferred embodiment, dehydrated nucleus tissue is used, which may be combined with extracellular matrix materials. The relative vascular isolation of the nucleus pulposis imparts isolation of nucleus pulposis cells from the body's immune system. This invention exploits the lack of an immune system response to the transplantation of nucleus pulposis cells and extracellular matrix harvested from another human or animal.

According to the method, the nucleus pulposis or other tissues are preferably harvested from a live human, though recently deceased human or animal donors may alternatively be used. Depending upon the extent of the harvest, the recipient may function at least in part as a donor, or the tissues from others, including fetal or embryo sources, may be used, preferably having a familial relationship to minimize or avoid the need for immunosuppressive substances. Guidelines for tissue procurement including surgical technique of removal, number of hours between death of the donor and tissue procurement, and testing of the donor for infectious disease, are well described in the literature.

Similarly, the guidelines for storage of living tissues are well known to those skilled in the art. The text "Organ Preservation for Transplantation" by Karow and Pego, 1981, describes such methods. Briefly, the tissue storage method must maintain cell viability and preserve sterility. Examples of present storage methods include: refrigeration, refrigeration with tissue culture medium such as: hemolyzed serum, autologous serum, Medium 199 with 5% dextran (McCarey-Kaufman medium), Medium 199 with chondroitin sulfate, Medium 199 supplemented with inorganic salts, short chain fatty acids, and/or ketone bodies, and cryopreservation techniques, among others. Details are provided in U.S. Pat. Nos. 4,695,536 and 4,873,186, the entire contents of which are incorporated herein by reference.

The tissue is dehydrated using known techniques. To minimize exposure to the recipient's immune system, the constituents are preferably inserted through a small hole in the annulus fibrosis using a blunt-tipped needle or cannula forced through the laminae. Upon withdraw of the needle, after injecting the transplanted nucleus pulposis, the separated fibers of the lamella return to their normal position, thereby sealing the annulus.

The annulus fibrosis is thicker in the anterior and lateral portion of the disc. Thus, in the preferred embodiment, the needle would be inserted into the anterior or lateral portion of the disc. Those skilled in the art will realize the needle could be directed into the lateral portion of the disc percutaneously with fluourscopic guidance and into the anterior portion of the disc laparoscopically.

The dehydrated materials may be morselized to allow insertion into the disc through a small cannula or needle. With respect to the nucleus pulposis, the increased surface area after morsellization may also aid diffusion of nutrients and wastes products to and from transplanted disc cells. Alternatively large sections of the transplanted nucleus pulposis could be added to the disc if the annular defect was sealed after transplantation.

The transplanted nucleus is preferably added to the patient's nucleus pulposis. Alternatively, the patient's nucleus could be removed with standard techniques (enzymatically (chymopapain) or with the aid of a laser, suction device, shaver, or other surgical instrument). If the nucleus is removed the hole in the annulus should be small and sealed to prevent the ingrowth of vascular tissue. Vascular ingrowth could lead to a graft versus host reaction.

Once in the body, the materials hydrate by imbibing fluid from the surrounding area. In the case of nucleus pulposis tissue, the subsequent hydration helps to restore disc height and help prevent extrusion of disc material through the hole in the annulus. Additional therapeutic substances may be added, including resorbable culture medium, tissue growth or differentiation factors (recombinant generated morphogenetic proteins, PDGF, TGF-$\beta$, EGF/TGF-$\alpha$, IGF-I, $\alpha$FGF), hydrogels, absorbable or nonresorbable synthetic or natural polymers (collagen, fibrin, polyglycolic acid, polylactic acid, polytetrafluoroethylene, etc.), antibiotics, anti-inflammatory medication, immunosuppressive medications, etc. could be beneficial. These additional substances may or may not be dehydrated as well, depending upon efficacy, initial versus final volume, and so forth.

I claim:

1. A method of treating a diseased or traumatized intervertebral disc having a nucleus and annulus fibrosis, comprising the steps of:

harvesting nucleus pulposis cells from a human or animal donor;

dehydrating the nucleus pulposis cells; and transplanting the dehydrated nucleus pulposis cells into the disc being treated.

2. The method of claim 1, further including the steps of:

morselizing the dehydrated tissue;

forming a passageway through the annulus fibrosis; and introducing the dehydrated cells matrix into the disc being treated through the passageway.

3. The method of claim 1, further including the step of adding one or more therapeutic substances to the dehydrated tissue prior to the implantation thereof.

4. The method of claim 3, wherein the therapeutic substances include one or more of the following:

culture media, growth factors, differentiation factors, hydrogels, polymers, antibiotics, anti-inflammatory medications, or immunosuppressive medications.

5. The method of claim 1, wherein the dehydrated tissue are injected into the disc being treated through a needle and syringe or small cannula.

6. The method of claim 1, wherein the dehydrated tissue is percutaneously or laparoscopically injected into the disc being treated.

7. The method of claim 1, further including the step of adding live nucleus pulposis cells to the dehydrated nucleus tissue.

* * * * *